US008690853B2

(12) United States Patent
Stepovich et al.

(10) Patent No.: US 8,690,853 B2
(45) Date of Patent: *Apr. 8, 2014

(54) METHODS AND APPARATUS FOR BUFFERING PARENTERAL SOLUTIONS

(71) Applicant: Onpharma, Inc., Los Gatos, CA (US)

(72) Inventors: Matthew J. Stepovich, Santa Cruz, CA (US); Michael I. Falkel, Carmel Highlands, CA (US)

(73) Assignee: Onpharma, Inc., Los Gatos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/631,241

(22) Filed: Sep. 28, 2012

(65) Prior Publication Data

US 2013/0085465 A1 Apr. 4, 2013

Related U.S. Application Data

(63) Continuation of application No. 12/833,702, filed on Jul. 9, 2010, now Pat. No. 8,303,566.

(60) Provisional application No. 61/270,571, filed on Jul. 9, 2009.

(51) Int. Cl.
*A61J 1/14* (2006.01)

(52) U.S. Cl.
USPC ............ 604/413; 604/403; 604/411; 604/414

(58) Field of Classification Search
None
See application file for complete search history.

(56) References Cited

U.S. PATENT DOCUMENTS

| 1,616,202 | A | | 2/1927 | Shook et al. |
| 1,757,809 | A | | 5/1930 | Montuori |
| 2,484,657 | A | | 10/1949 | Son |
| 2,604,095 | A | | 7/1952 | Brody |
| 3,753,432 | A | * | 8/1973 | Guerra .......................... 600/577 |
| 3,993,751 | A | | 11/1976 | Zinke |
| 3,993,791 | A | | 11/1976 | Breed et al. |
| 4,154,820 | A | | 5/1979 | Simoons |

(Continued)

FOREIGN PATENT DOCUMENTS

EP 0298067 A1 1/1989

OTHER PUBLICATIONS

International search report and written opinion dated Sep. 13, 2010 for PCT Application No. US2010/041613.

(Continued)

*Primary Examiner* — Jackie Ho
*Assistant Examiner* — Eric Bryant
(74) *Attorney, Agent, or Firm* — Wilson Sonsini Goodrich & Rosati

(57) ABSTRACT

A system for transferring solutions from a first cartridge into a second cartridge comprises a cartridge holder, a plunger driver, and a cartridge connector. The cartridge connector carries a transfer needle and an exhaust needle. The cartridge holder positions the first cartridge against the cartridge connector so that the transfer needle penetrates the first cartridge septum. The second cartridge is removably inserted into another end of the cartridge connector so that both the transfer needle and the exhaust needle penetrate the second cartridge septum. The plunger driver is disposed to advance a plunger on the first cartridge to transfer solution from the first cartridge into the second cartridge thus displacing solution from the second cartridge through the exhaust needle. The cartridge connector includes a sealed interior waste chamber for receiving the solution from the second cartridge.

17 Claims, 4 Drawing Sheets

(56) References Cited

U.S. PATENT DOCUMENTS

| | | | |
|---|---|---|---|
| 4,259,956 A | 4/1981 | Ogle | |
| 4,513,015 A | 4/1985 | Clough | |
| 4,630,727 A | 12/1986 | Feriani et al. | |
| 4,654,204 A | 3/1987 | copenhafer et al. | |
| 4,704,088 A | 11/1987 | Newman | |
| 4,756,838 A | 7/1988 | Veltman | |
| 4,795,441 A | 1/1989 | Bhatt | |
| 4,808,169 A * | 2/1989 | Haber et al. | 604/195 |
| 4,959,175 A | 9/1990 | Yatzidis | |
| 5,062,832 A | 11/1991 | Seghi | |
| 5,137,528 A | 8/1992 | Crose | |
| 5,143,084 A | 9/1992 | Macemon et al. | |
| 5,149,320 A | 9/1992 | Dhaliwal et al. | |
| 5,226,901 A | 7/1993 | Dhaliwal et al. | |
| 5,261,903 A | 11/1993 | Dhaliwal et al. | |
| 5,296,242 A | 3/1994 | Zander | |
| 5,318,544 A | 6/1994 | Drypen et al. | |
| 5,330,426 A | 7/1994 | Kriesel et al. | |
| 5,358,489 A * | 10/1994 | Wyrick | 604/136 |
| 5,383,324 A | 1/1995 | Segers et al. | |
| 5,542,934 A | 8/1996 | Silver | |
| 5,603,695 A | 2/1997 | Erickson | |
| 5,609,572 A | 3/1997 | Lang | |
| 5,609,838 A | 3/1997 | Neuman et al. | |
| 5,610,170 A | 3/1997 | Inoue et al. | |
| 5,690,215 A | 11/1997 | Kimball et al. | |
| 5,779,357 A | 7/1998 | Jonsson et al. | |
| 5,840,252 A | 11/1998 | Giertych | |
| 5,984,906 A | 11/1999 | Bonnichsen et al. | |
| 6,022,337 A | 2/2000 | herbst et al. | |
| 6,232,128 B1 | 5/2001 | Iguchi et al. | |
| 6,620,138 B1 | 9/2003 | Marrgi et al. | |
| 6,692,468 B1 | 2/2004 | Waldenburg | |
| 6,723,068 B2 * | 4/2004 | Lavi et al. | 604/82 |
| 6,948,522 B2 | 9/2005 | Newbrough et al. | |
| 7,462,164 B2 | 12/2008 | Moir | |
| 8,303,566 B2 * | 11/2012 | Stepovich et al. | 604/413 |
| 2004/0175437 A1 | 9/2004 | Beckett | |
| 2005/0113747 A1 | 5/2005 | Moir | |
| 2007/0265593 A1 | 11/2007 | Kitagawa et al. | |
| 2008/0045925 A1 | 2/2008 | Stepovich et al. | |
| 2009/0221984 A1 | 9/2009 | Girgis et al. | |
| 2009/0292271 A1 | 11/2009 | Stepovich et al. | |

OTHER PUBLICATIONS

Michaels. Sterilisation of sodium bicarbonate solutions. Pharm J. Sep. 4, 1948; 107(4427):160-161.

Office action dated May 29, 2012 for U.S. Appl. No. 12/833,702.

* cited by examiner

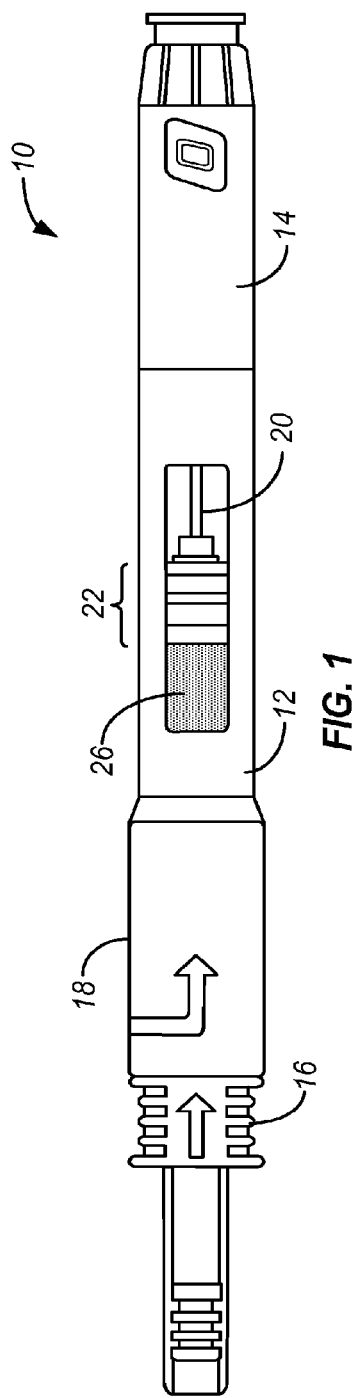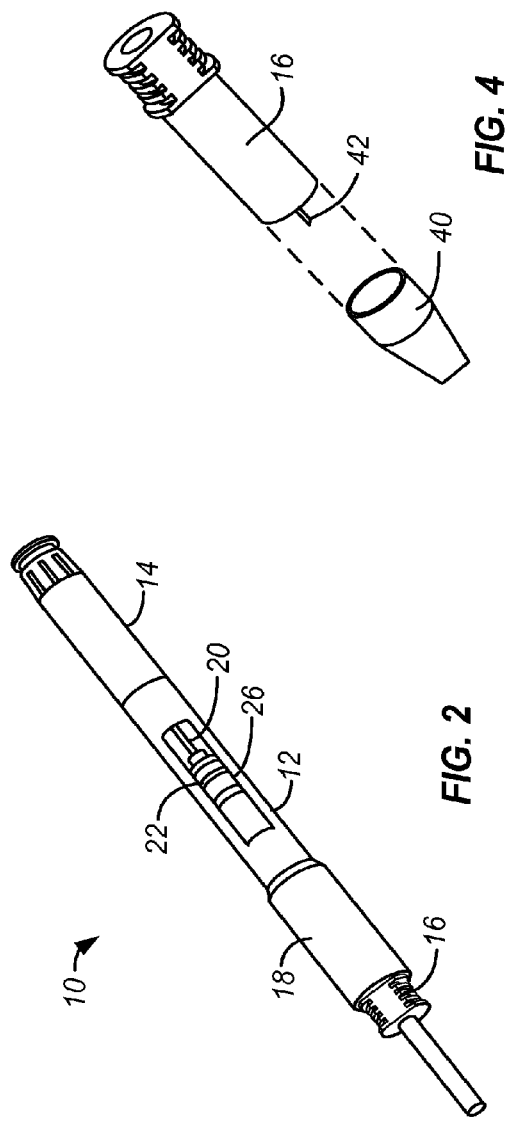

METHODS AND APPARATUS FOR BUFFERING PARENTERAL SOLUTIONS

CROSS-REFERENCES TO RELATED APPLICATIONS

This application is a continuation of U.S. patent application Ser. No. 12/833,702, filed Jul. 9, 2010, which claims the benefit of prior provisional application 61/270,571, filed on Jul. 9, 2009, the full disclosure of which is incorporated herein by reference. The present application is also related to, but does not claim the benefit of, U.S. patent application Ser. No. 12/406,670, filed on Mar. 18, 2009, now issued U.S. Pat. No. 8,162,917, the full disclosure of which is incorporated herein by reference.

BACKGROUND OF THE INVENTION

1. Field of the Invention

The present invention relates generally to methods and apparatus for combining parenteral solutions. More particularly, the present invention relates to methods for combining sodium bicarbonate and other buffering solutions with parenteral solutions stored in small cartridges.

Solutions containing bicarbonate ions are used in various medical applications such as antidotes, dialysates, artificial cerebrospinal fluid, intraocular irrigating solutions, cardiac perfusates, cardioplegic solutions, peritoneal irrigating solutions, and solutions for organ preservation, etc. Of particular interest to the present application bicarbonate solutions are used to buffer the pH dental anesthetic and other parenteral solutions. One of the most commonly used medical bicarbonate solutions consists of sodium bicarbonate ($NaHCO_3$) mixed with water ($H_2O$). In medical bicarbonate solutions, bicarbonate ions are in equilibrium as represented by the following expression:

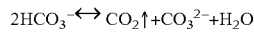

$$2HCO_3^- \leftrightarrow CO_2\uparrow + CO_3^{2-} + H_2O$$

If the reaction occurs in a closed system, equilibrium is between the partial pressure of carbon dioxide in solution and the partial pressure of carbon dioxide in any space over the solution. In open systems at atmospheric pressure and room temperature, for instance where a beaker of sodium bicarbonate solution is left open in a lab environment, carbon dioxide gas will continue to leave solution until the reaction has proceeded almost completely to the right, or until almost all the bicarbonate ($2HCO_3$) has evolved into carbon dioxide gas ($CO_2$), carbonate ($CO_3$) and water ($H_2O$), and where all the $CO_2$ gas has left the open beaker and entered the ambient air in the lab. Bicarbonate is more acid than carbonate, meaning that the pH of the solution will have progressively moved toward the alkaline side of the pH scale. In fact, under these circumstances, the bicarbonate solution will achieve a pH over 9.5.

All commercially available medical sodium bicarbonate solutions are supplied sterile in closed containers. All of them also have some amount of headspace into which, presumably, $CO_2$ could evolve out of solution until an equilibrium between $CO_2$ evolving out of solution and going back in to solution, per the above equation, is reached. It could therefore be hypothesized that the commercially available sodium bicarbonate solutions have a pH that could exist in a fairly wide range. In fact the labels on all commercially available medical bicarbonate solutions state, per the United States Pharmacopeia guidelines, that the pH can be anywhere from 7.0 to 8.5. An assay of a sample set of commercially available medical sodium bicarbonate solutions in a variety of volumes and containers may have pH range from 7.6 to 8.3 or more.

The pH of bicarbonate solutions is thus not a fixed figure, but rather can exist at a range of levels dictated by the factors that tend to push the equilibrium equation, in a particular environment, either to the right or to the left, principally controlled by $CO_2$ leaving or entering solution.

Notably, in a closed container with no headspace, the pH of sodium bicarbonate solution can be fixed by placing the solution having a known starting pH, in a sealed container under pressure that exceeds the partial pressure of $CO_2$ in the solution, without a headspace. In that environment, $CO_2$ will not evolve out of solution because pressure on the solution is greater than the partial pressure of $CO_2$, and therefore the pH will not rise. Also in this environment where the pressure being exerted on the solution is greater than the partial pressure of $CO_2$ in solution, because there is no headspace, and hence no available $CO_2$ gas that can be driven into solution, the pH of the solution will not decrease. In this model then, $CO_2$ does not leave or enter solution and, accordingly, the pH does not have the opportunity to either rise or fall. The pH of the solution in this system, is therefore, essentially fixed once the system is closed.

Even if the pH is known and fixed within a sealed container, a significant pH change can be caused by the process of transferring the bicarbonate solution out of the container. Where the bicarbonate solution is to be combined with another solution, as in anesthetic buffering, the process of mixing two solutions together can also include steps that will create a greater or lesser pH change, which can affect the predictability of the buffering process.

These considerations are important in buffering parenteral solutions using a syringe with a hypodermic needle to "draw up" bicarbonate solution from a vial having a pierceable septum, and then mixing the bicarbonate with the target solution in order to alter the pH of the target solution. This vial and syringe system is typical and allows a practitioner to remove multiple doses of solution from a container without opening the container or exposing it to the ambient air. Vials that are intended to be used in this manner necessarily include a significant headspace, without which drawing up fluid in this manner could not occur. When the vial contains a headspace, as the practitioner withdraws the syringe's plunger, the headspace can expand to fill the space vacated by the liquid that is leaving the vial, traveling through the hypodermic needle, and entering the barrel of the syringe. Of course, as more and more solution is drawn up, for instance as multiple doses of the solution are used, the headspace expands more and more, continually lowering the gas pressure in that headspace.

Where a vial of this type contains bicarbonate that is removed in doses using a syringe, over time, because the partial pressure of the gas in the headspace drops, the partial pressure of $CO_2$ in the headspace drops as well, taking it out of equilibrium with the partial pressure of the $CO_2$ in solution. Per the equation set forth earlier, $CO_2$ gas will evolve out of solution to re-establish the equilibrium, which has the effect of raising the pH of the bicarbonate solution each time a volume of the solution is drawn up into a syringe. Whatever the starting pH of the vial's bicarbonate solution may have been, if it were known, the pH of the solution in the vial, after any amount of the solution has been removed in this manner, cannot be known. Therefore, if the pH of the solution is an important element of its clinical utility, as when the bicarbonate is to be used for buffering the pH of a target solution such as anesthetic, withdrawing bicarbonate from a vial using a syringe may alter the pH to a degree that makes it difficult to predictably buffer any parenteral solution using this method.

Another concern when bicarbonate solution is drawn from a vial using a syringe is the effect of the vacuum created in the fluid path that leads from the bicarbonate vial to the syringe. It has been observed that it is nearly impossible to draw up solution from a vial into a syringe using a needle in the range typically employed for injections (25-30 gauge) without creating gas in the syringe during the process. This is because the act of drawing the solution into the syringe creates a vacuum on that solution that causes significant $CO_2$ to evolve out of the solution that is being transferred. The resulting pH change, along with the pH change that is occurring inside the vial with every withdrawal of a dose of bicarbonate from the vial itself means that it is impossible to know what the pH of the bicarbonate solution being used as a buffer is. With that lack of knowledge, the practitioner cannot control for the key variable that would inform him or her as to how much bicarbonate solution should be used in the buffering process. For this reason, buffering anesthetic using a vial of bicarbonate and a hypodermic syringe is akin to a "home brew" where the results are not predictable and, in the case where the pH of the bicarbonate is too high, could buffer the anesthetic into a range where it can precipitate out of solution, making the buffered anesthetic dangerous.

Commonly-owned copending application US 2009/0292271 (application Ser. No. 12/406,670, previously incorporated herein by reference) describes a "dosing pen" device capable of combining buffers and anesthetics and overcoming many of the shortcomings of the prior art described above. The '271 application discloses a fluid transfer device which utilizes a transfer needle 36 and an exhaust needle 38 positioned in a knob 12 which can removably receive an anesthetic cartridge 28 so that distal ends of both the transfer needle and exhaust needle penetrate a septum on the anesthetic cartridge. A buffer cartridge 16 positioned within a housing 14 is also attached to the knob 12 so that a proximal end 50 of the transfer needle 36 can penetrate a septum 15 of the buffer cartridge when the knob is fully advanced onto the housing. A pusher 20 is provided to drive a plunger 58 on the buffer cartridge to transfer buffer through transfer needle 36 into the anesthetic cartridge 28 and to simultaneously exhaust anesthetic from the anesthetic cartridge back into a reservoir 72 in the housing 14 through the exhaust needle 38.

While the dosing pen of the '271 application is advantageous in many respects, some improvements can be made such that a similar pen will provide additional benefits. First, the dosing pen is designed to hold a single buffer cartridge 16, and the design of the pen makes it difficult to replace the buffer cartridge. In particular, the pusher 20 is attached to the housing 14 to position an intermediate spring 18 against the plunger of the buffer cartridge, and a mechanism is provided which defines two advancement strokes to allow transfer of two pre-defined volumes of buffer to one or two anesthetic cartridges. The pusher assembly is not easily disassembled, making replacement of the buffer difficult. Thus, the entire pen must be disposed of after use.

Second, the pusher mechanism described above does not allow free selection of a range of transfer volumes prior to use. The pusher mechanism only allows two pre-defined volumes to be transferred by any particular pen construction. It would be desirable to allow a user to select or "dial in" any volume in a given range without being limited to specific preset values.

Third, the excess buffer, which is exhausted through exhaust needle 38, ends up in the housing 14. While it is theoretically possible to empty the buffer and clean the housing (assuming the device could be disassembled, which is difficult), it would be preferable if the excess buffer were exhausted into another component of the system which could either be more easily cleaned or be disposed of while allowing other components to be reused.

Fourth, removal of the first buffer cartridge from the dosing pen of the '271 application can be done without having removed the transfer needle from the buffer cartridge. Having a needle that can be left in a position where it provides a fluid path open to the ambient air (that is penetrating the septum of the buffer cartridge) could allow carbon dioxide to evolve out of solution, thus potentially affecting the pH of the buffer.

For these reasons, it would be desirable to provide improved methods and apparatus for combining buffer solutions with anesthetics, particularly where the buffer solutions and/or anesthetics are held in conventional glass cartridges with needle penetrable septums and dispensing plungers. It would be further desirable if such methods and apparatus could be used with other parenteral and medical solutions which are desired to be combined under carefully controlled conditions. The methods and devices would preferably allow for convenient buffering or dosing of multiple anesthetic or other cartridges from a single buffer or other medical solution cartridge. It would be still further desirable if the methods and devices provided for a removal of a transfer needle from the buffer or other medical solution cartridge every time the anesthetic or other recipient cartridge was removed from the dosing apparatus. Still further, it would be desirable if some components of the apparatus were reusable and the buffer cartridges replaceable. At least some of these objectives will be met by the inventions described hereinbelow.

2. Description of the Background Art

US2009/0292271 has been described above. Glass vials and cartridges for storing medical solutions are described in U.S. Pat. Nos. 1,757,809; 2,484,657; 4,259,956; 5,062,832; 5,137,528; 5,149,320; 5,226,901; 5,330,426; and 6,022,337. Injection pens which employ drug cartridges are described in U.S. Pat. No. 5,984,906. A particular disposable drug cartridge that can find use in the present invention is described in U.S. Pat. No. 5,603,695. A device for delivering a buffering agent into an anesthetic cartridge using a transfer needle is described in U.S. Pat. No. 5,603,695. Devices for maintaining a dissolved gas in solution in a pouch are described in U.S. Pat. Nos. 5,690,215; 5,610,170; and 4,513,015, and U.S. Patent Publ. No. 2007/0265593. Other patents and applications of interest include U.S. Pat. Nos. 2,604,095; 3,993,791; 4,154,820; 4,630,727; 4,654,204; 4,756,838; 4,959,175; 5,296,242; 5,383,324; 5,603,695; 5,609,838; 5,779,357; and U.S. Patent Publ. No. 2004/0175437.

BRIEF SUMMARY OF THE INVENTION

The present invention provides methods and apparatus for combining medical or parenteral solutions, such as buffering anesthetics or other medical or parenteral solutions held in a conventional cartridge, particularly those having a penetrable septum and a slidable plunger or plug, such as those generally described in US 2009/0292271, the full disclosure of which is incorporated herein by reference. Such cartridges are commonly used in dental practice, particularly for delivering anesthetics to a patient prior to a procedure. Such cartridges are conventionally loaded into a syringe or other delivery device, where the syringe engages the plunger in the cartridge to dispense the anesthetic through a needle which has penetrated the septum. To optimize effectiveness of the anesthetics and to reduce injection pain, it is desirable to buffer conventional dental anesthetics, typically lidocaine, articaine, prilocalne, or mepivacaine, shortly before use. It is very important, however, that the buffering solutions themselves have predictable, stable pHs and chemical compositions in order to accurately, reliably, and safely buffer anesthetic to achieve a much more rapid onset, optimum effectiveness, and minimum injection pain.

Methods according to the present invention for buffering anesthetic cartridges comprise providing a buffer cartridge having a septum and a plunger and providing an anesthetic cartridge having a septum and a plunger. The plunger end of the buffer cartridge is attached to one end of a cartridge connector so that a transfer needle which is part of the cartridge connector penetrates the septum of the buffer cartridge to establish a flow path out of said cartridge. A septum end of the anesthetic cartridge is attached to the other end of the cartridge connector so that the transfer needle and an exhaust needle both penetrate the septum of the anesthetic. The transfer needle thus provides a transfer flow path from the buffer cartridge to the anesthetic cartridge, while as described in more detail below, the exhaust needle provides a flowpath from the anesthetic cartridge to a sealed interior waste chamber in the cartridge connector. By "sealed interior waste chamber" it is meant that the waste chamber will receive and hold excess volumes of the anesthetic which are displaced when buffer is transferred into the anesthetic cartridge. Usually, the chamber will have at least a small gas exhaust path to allow gas to bleed from the waste chamber as the liquid anesthetic enters the chamber.

In this way, when the user advances the buffer cartridge plunger to transfer a volume of buffer from the buffer cartridge into the anesthetic cartridge, a like volume of anesthetic will be displaced from the anesthetic cartridge into the waste chamber in the cartridge connector where it will be sequestered until the cartridge connector is emptied or disposed of.

It is a particular advantage of the present invention that the anesthetic cartridge may be removed from the cartridge connector after a desired volume of buffer has been transferred from the buffer cartridge to the anesthetic cartridge. In particular, the cartridge connector can be configured so that the transfer needle must be removed from the buffer cartridge before the anesthetic cartridge can be removed from the cartridge connector. In this way, the buffer remains sealed (the septum seals after the transfer needle is removed) within the buffer cartridge and is not exposed to the ambient or atmosphere through the transfer needle when the anesthetic cartridge has been removed and the remote end of the transfer needle is open to the atmosphere. Once the anesthetic cartridge has been removed, the cartridge connector and other apparatus remain available for attachment to a second anesthetic cartridge for an extended period of time, since the buffer remains sealed within the buffer cartridge. After a second anesthetic cartridge is attached again to the cartridge connector, the plunger on the upper cartridge may be further advanced to transfer an additional volume of buffer to the second anesthetic cartridge. The second anesthetic cartridge can then be removed from the cartridge connector with the transfer needle again being withdrawn from the septum of the buffer cartridge to preserve the pH of the buffer and additional anesthetic cartridges inserted until the buffer is used up.

The methods of the present invention further allow for different volumes of buffer to be delivered to the different anesthetic cartridges which are sequentially replaced and attached to the cartridge connector. For example but not by way of limitation, volumes in 0.01 increments in the range from 0.01 ml to 0.60 could be selected and "dialed in" to a device which advances the buffer cartridge plunger to deliver any volume increment in that range, in contrast to the limited number of pre-selected volumes deliverable by the devices of the '271 application discussed above.

In a still further aspect of the present invention, the amount of buffer remaining in the buffer cartridge will be visible to the user so that the same buffer cartridge can be used multiple times until the buffer cartridge is empty, or until so small a volume remains that it is no longer usable. In such cases, the cartridge connector will have collected a significant volume of anesthetic of other parenteral solution being buffered. It will usually be desirable to dispose of the cartridge connector and to later employ a new, sterile cartridge connector with other components of the system (as described below).

In particular aspects of the methods of the present invention, the cartridge connector is manipulated by removably attaching the connector to a cartridge holder which holds the buffer cartridge. The cartridge connector is thus attached at one end to the cartridge holder and includes a sleeve or receptacle at the other end for removably receiving the anesthetic cartridge. Usually, the cartridge holder will have a window which allows visual observation of the contents of the buffer cartridge during use. A separate plunger driver may be attached to an opposite end of the cartridge holder for engaging a plunger on the buffer cartridge to controllably dispense and transfer preselected volumes of the buffer to the anesthetic cartridge.

The present invention further provides devices for transferring a volume of solution from a first cartridge having a septum to another solution in a second cartridge having a septum. The device comprises a cartridge holder, a plunger driver, and a cartridge connector. The cartridge holder has a proximal end, a distal end, and a chamber for removably receiving the first cartridge, which is typically a buffer, such as a sodium bicarbonate buffer as described in more detail above. The plunger driver is attachable to the proximal end of the cartridge holder and has a piston rod which engages a plunger on the first cartridge, where the piston rod is controllable to axially advance the plunger to deliver pre-selected "dialed-in" volumes of the content of the first cartridge. Such plunger drivers are commercially available from suppliers such as Haselmeier GmbH, St. Gallen, Switzerland. As used in the present invention, such plunger drivers will have a mechanism which allows a variable volume to be selected and delivered, typically by rotating a knob which displays the volume in a window, and further includes a button which may be depressed for advancing the piston rod to cause the piston rod to travel a distance which will dispense the desired volume of liquid from the first cartridge.

The cartridge connector of the present invention has a proximal end which is attachable to the distal end of the cartridge holder and a distal end which is adapted to engage a septum end of the second cartridge. The cartridge connector will further have a sealed interior waste chamber and includes a transfer needle and an exhaust needle. The transfer needle extends from one end of the cartridge connector to the other so that it will penetrate through a septum of the first (e.g. buffer) cartridge at one end and through a septum of the second (e.g. anesthetic) cartridge at the other end. The exhaust needle extends from the second cartridge and terminates within the interior waste chamber. In this way, as described in connection with the method of the present invention, advancement of the plunger in the first cartridge transfers solution into the second cartridge and further causes the solution in the second cartridge to be exhausted through the exhaust needle into the interior waste chamber.

The cartridge holder has a body, typically cylindrical, with a window to allow visual observation of the contents of the cartridge in the cartridge holder. In this way, the user can see when the first cartridge is running low and needs to be replaced. A distal region of the cylindrical body is typically enlarged to removably receive the cartridge connector, and the cartridge connector will typically be interlocked so that the transfer needle can penetrate the first cartridge (held within the cartridge holder) only when the second cartridge is placed over the other end of the transfer needle.

The cartridge connector will usually also comprise a cylindrical body, and the cylindrical body will typically be removably received within the enlarged end of the distal region of the cartridge holder. The sealed interior waste chamber of the cartridge connector is defined between spaced-apart walls in the cylindrical body of the cartridge connector, and usually a first end of the cylindrical body will form a cylindrical sleeve which surrounds the exposed ends of the exhaust needle and the transfer needle, where the sleeve is adapted to removably receive the septum end of the second cartridge.

The present invention still further provides a cartridge connector for providing or establishing fluid transfer paths between a first cartridge having a septum and a second cartridge having a septum. The cartridge connector comprises a body having a first end, a second end, and a sealed interior waste chamber. A transfer needle has a first end exposed at a first end of the body and a second end exposed at a second end of the body. Both the first and second ends of the transfer needle are capable of penetrating a cartridge septum. An exhaust needle is provided on the body and has a first end exposed at the first end of the body and a second end terminating in the sealed interior waste chamber. At least the first end of the exhaust needle is capable of penetrating a cartridge septum.

The first end of the cartridge connector will typically include a cylindrical sleeve or similar structure surrounding the exposed ends of the transfer needle and the exhaust needle. The cylindrical sleeve will be adapted to removably receive the septum of a cartridge, typically an anesthetic cartridge. Usually, the first end of the transfer needle is axially spaced-apart from the first end of the exhaust needle so that the material being exhausted will be segregated from the material being transferred in through the transfer needle. Usually, the transfer needle will be axially or otherwise disposed through the sealed interior waste chamber, and the second end of the transfer needle will be free from surrounding structure. Usually, the cartridge connector will be provided as a separate sterile component of the devices and systems described herein and will be provided with a separate removable cap for placing over the exposed second end of the transfer needle for safety.

BRIEF DESCRIPTION OF THE DRAWINGS

FIG. 1 is a side view of a dosing pen system constructed in accordance with the principles of the present invention and having a buffer cartridge and an anesthetic cartridge attached.

FIG. 2 is a perspective view of the dosing pen system of FIG. 1.

FIG. 4 illustrates the cartridge connector of the dosing pen system of FIGS. 1-3, including a safety cap for protecting an exposed end of a transfer needle.

DETAILED DESCRIPTION OF THE INVENTION

Figure 3:
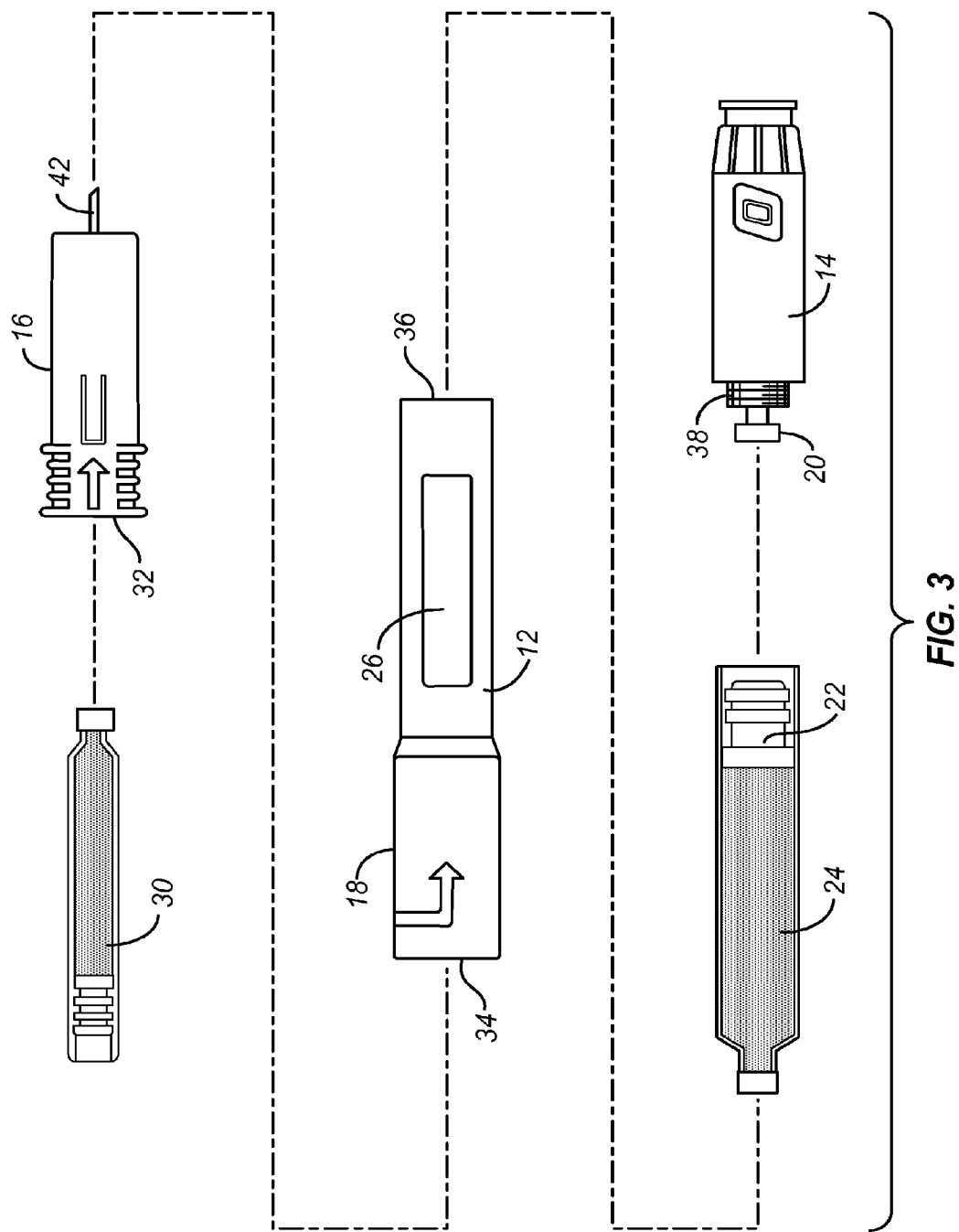
FIG. 3 is an exploded view of the dosing pen system of FIGS. 1 and 2 illustrating each of the components separately.

As shown in FIGS. 1 and 2, a dosing pen system 10 includes a cartridge holder 12, a plunger driver 14, and a cartridge connector 16. The cartridge connector 16 is removably received in an enlarged distal end 18 of the cartridge holder 12, and the plunger driver 14 includes a piston rod 20 which drives a plunger 22 on a first (buffer) cartridge 24 (best seen in FIG. 3) which is observable through a window 26 through a wall of the cartridge holder 12.

The plunger driver 14 may be obtained as a pre-assembled unit from commercial vendors. In particular, Haselmeier GmbH, article number 435300, is suitable for use in the present invention.

Referring now to FIG. 3, an anesthetic cartridge 30 is inserted through a distal end 32 of the cartridge connector 16, as will be described in greater detail below with respect to FIGS. 5-7. The cartridge connector 16, in turn, is inserted in through distal end 34 of the cartridge holder 12 so that it is received in the enlarged distal end 18. The buffer cartridge 24 is inserted in through a proximal end 36 of the cartridge holder 12 so that it is visible through the window 26 and a septum end penetrates needles of the cartridge connector 16, as described in more detail with respect to FIGS. 6 and 7 below. Finally, the plunger driver 14 is attached to the proximal end 36 of the cartridge holder 12, typically using a threaded or similar connector 38 at a distal end of the plunger driver. With all the connections just described, the dosing pen 10 is in the configuration illustrated in FIGS. 1 and 2.

Figure 5:
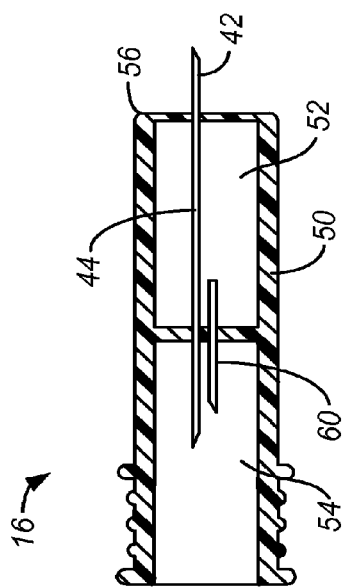
FIG. 5 is an axial cross-sectional view of the cartridge connector of the dosing pen of the present invention illustrating the relative positions of the transfer needle, the exhaust needle, and a sealed interior waste chamber thereof.
Figure 6:
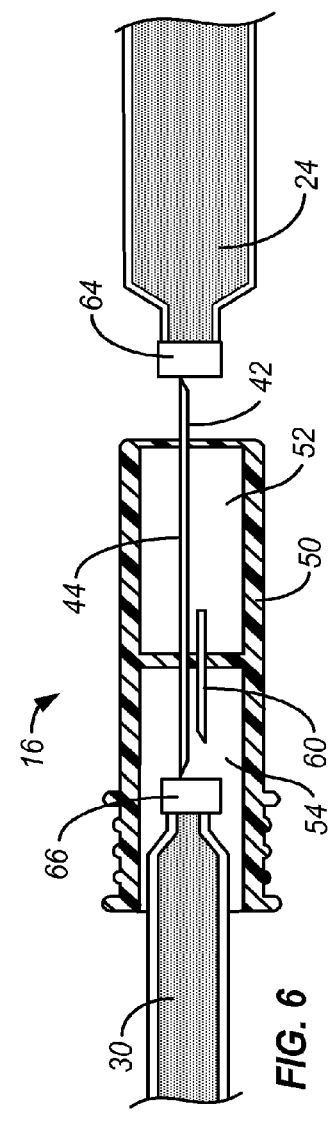
FIGS. 6 and 7 illustrate the attachment of a first (buffer) cartridge and a second (anesthetic) cartridge to the cartridge connector of FIG. 5.
Figure 7:
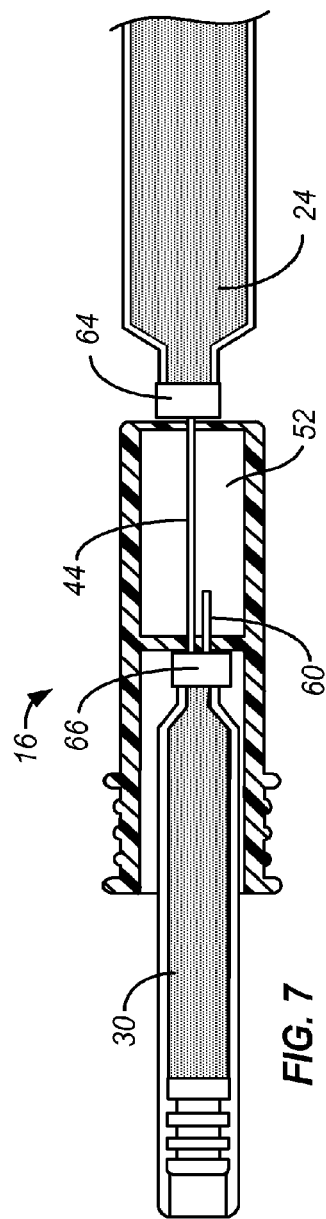

Referring now to FIG. 4, the cartridge connector 16 will typically be provided with a removable cover or cap 40 which protects an exposed end 42 of transfer needle 44, as seen in FIGS. 5-7. The cap 40 is provided to protect personnel handling the connector. Typically, the cartridge connector 16 will be provided as a sterile component with the cap 40 attached over the exposed end 42 of needle 44, usually in a sterile pack, such as a pouch. The remaining components of the dosing pen, and in particular the cartridge holder 12 and the plunger driver 14 will typically be reusable and will not need to be maintained in or returned to a sterile condition. Typically, cleaning with conventional cleaning agents is sufficient between successive uses. As the cartridge connector 16 is the only system component which directly contacts the buffer, anesthetic, or other parenteral solutions, the sterility of these solutions can be maintained so long as the sterility of the cartridge connector is maintained.

Referring now to FIG. 5, the cartridge connector 16 comprises a cylindrical body 50, typically formed from a molded plastic such as ABS, and includes at least one interior chamber 52 (which may be divided into more chambers and/or may include vents, membranes, absorptive materials or other features). The cylindrical body 50 will also usually include an open region or sleeve segment 54 which is adapted to receive the septum end of the anesthetic cartridge 30. The transfer needle 44 extends from proximal end 56 of the cylindrical body 50 to a position within the interior of the open region 54.

An exhaust needle 60 has one end within the open region 54 and another end terminating within the sealed chamber 52. Sealed chamber 52 will receive anesthetic or other solution which is being exhausted from the first cartridge 30 as buffer or other solutions are transferred into the first cartridge. The sealed chamber 52 will typically be liquid tight but may have gaseous exhaust paths so that the liquid may fill the chamber while exhausting air or other gases initially present within the chamber. Such exhaust paths can be provided by having capillary exhaust paths formed in the chamber which allow gas to vent while preventing liquid passage.

As shown in FIGS. 6 and 7, the buffer cartridge 24 is attached to the exposed end 42 of transfer needle 44 by advancing the sharpened end of the needle through the septum end 64 of the first cartridge, as shown in FIG. 7. Similarly, the septum end 66 of the second cartridge 30 is advanced over the ends of the transfer needle 44 and exhaust needle 60, as shown in FIG. 7.

In a specific aspect of the present invention, attachment of the second (anesthetic) cartridge 30 to the transfer needle 44 and exhaust needle 60 can be interlocked with the presence of the exposed end 42 of the transfer needle in the first (buffer) cartridge 44. In particular, it is desirable that the transfer needle 44 be removed from the first cartridge if and when the second cartridge is removed from the cartridge connector. This can be achieved, for example, by providing a series of force fit connections of declining relative strength between the second cartridge and the cartridge connector 16. Thus, when the practitioner pulls the second cartridge distally away from the cartridge connector 16 and first cartridge 24, the force fit between the cartridge connector housing and the first cartridge 24 is first to release because it is the weakest force fit. This allows the transfer needle to move away from the first cartridge and disconnect from the first cartridge after a dosing event. The transfer needle may travel until it hits a distal stop. When the transfer needle can no longer move distally, the second cartridge will disconnect from the cartridge connector. When another second (anesthetic) cartridge is connected to the cartridge connector 16, the process of inserting the transfer needle back into the buffer cartridge can be reversed. In this way, when no second (anesthetic) cartridge is present when the transfer needle is open to the atmosphere, the transfer needle will necessarily have been removed from the first (buffer) cartridge so that the pH cannot be disturbed.

Figure 8:
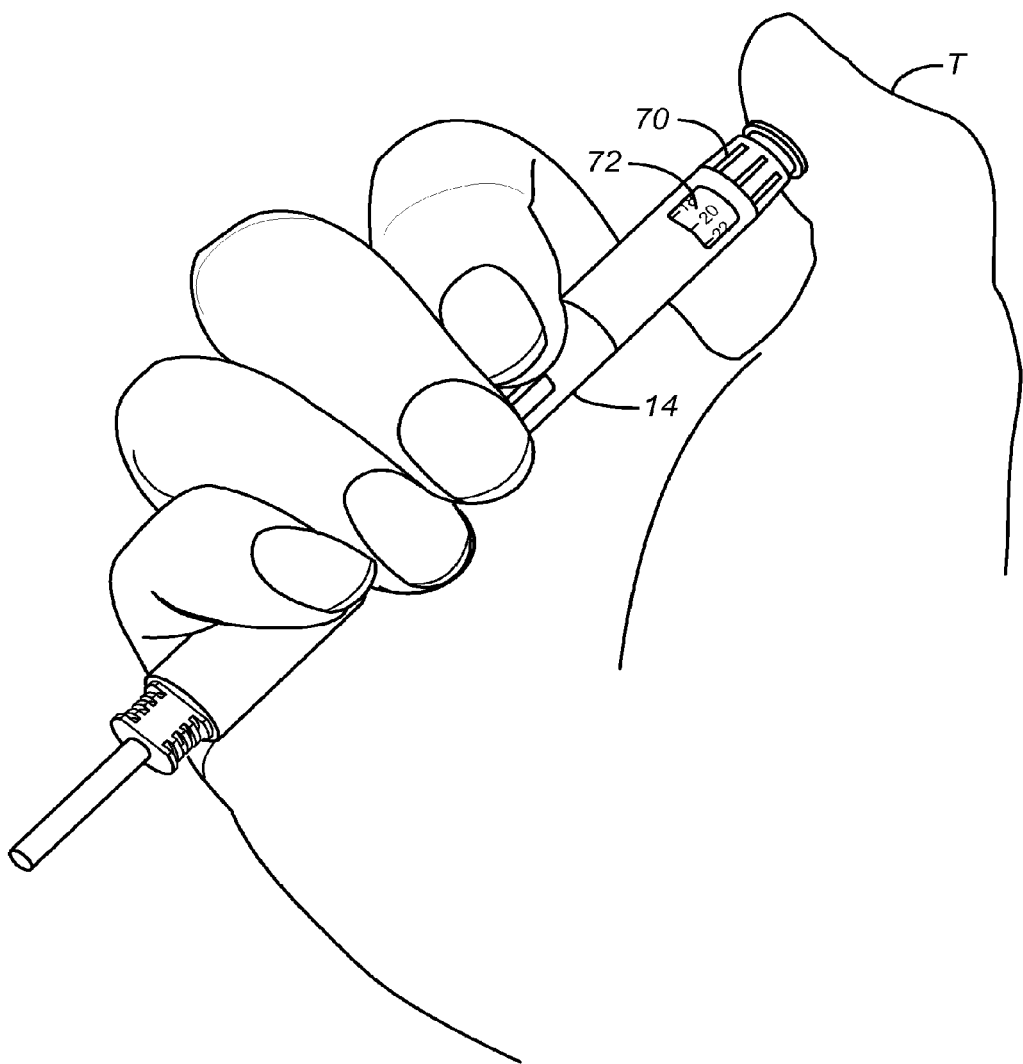
FIG. 8 illustrates the manual actuation of the dosing pen system of the present invention.

Referring to FIG. 8, a user can transfer buffer or other parenteral solution to an anesthetic or other parenteral solution by connecting the cartridges 24 and 30 to the cartridge connector 16 as generally shown in FIGS. 1-3, 6, and 7. The user then turns knob 70 on the plunger driver 14 to choose the desired transfer volume, as shown in window 72. Once the volume is "dialed in", the user can press the knob 40 using thumb T in order to advance the piston rod 20 a distance determined by the knob rotation which corresponds to the desired volume. After transferring a desired target volume of buffer or other solution into cartridge 30, the cartridge 30 may be removed and replaced with another cartridge to which the buffer or other solution is to be transferred. The desired transfer volume can then be dialed in and the knob depressed to transfer the buffer to the second cartridge. This process can be continued with further cartridges until the volume of buffer or other solution in cartridge 24 is depleted, as can be seen through window 24 when plunger 22 reaches the far left of the window 26, as shown in FIG. 1.

Figure 9:
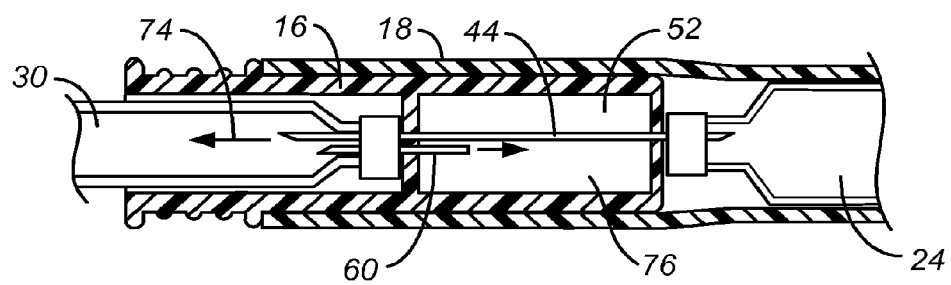
FIG. 9 illustrates the fluid transfer flow between a first (buffer) cartridge, second (anesthetic) cartridge, and sealed interior waste chamber caused by the manual actuation of the dosing pen system.

As shown in FIG. 9, depressing the plunger causes buffer or other solution from cartridge 24 to flow through transfer needle 44 and into cartridge 30, as indicated by arrow 74. As the cartridge 30 has a fixed volume and is usually full of fluid, the entry of buffer or other fluid will cause an excess volume which is exhausted through exhaust needle 60, in the direction of arrow 76. The ends of transfer needle 44 and exhaust needle 60 may be offset from each other, to the degree shown or to a greater or lesser degree, so that solution that is delivered by transfer needle 44 is limited in its tendency to be captured and expelled through exhaust needle 60. Exhaust chamber 52 can receive a significant volume of the exhausted anesthetic or other solution before it is full. After it is full, it either needs to be disposed of or emptied.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A device for transferring a volume of a solution from a first cartridge having a septum to another solution in a second cartridge having a septum, said device comprising:
   a cartridge holder having a proximal end, a distal end, and a chamber for removably holding the first cartridge;
   a plunger driver removably attachable to the proximal end of the cartridge holder and having a piston rod which engages a plunger on the first cartridge; and
   a cartridge connector having a proximal end attachable to the distal end of the cartridge holder, a distal end adapted to engage a septum end of the second cartridge, said cartridge connector including a transfer needle and an exhaust needle which extend distally to penetrate the septum end of the second cartridge, wherein the transfer needle extends proximally to penetrate the septum of the first cartridge and the exhaust needle terminates in the sealed interior waste chamber;
   wherein after use, the plunger driver may be removed from the cartridge holder, the first cartridge removed, and the cartridge holder and plunger cleaned for re-use.

2. A device as in claim 1, wherein the cartridge connector has an interior waste chamber which is configured to receive waste solution from the second cartridge which is displaced from the second cartridge as fluid from the first cartridge is transferred.

3. A device as in claim 1, wherein the cartridge holder has a cylindrical body with a window to allow visual observation of the contents of the first cartridge in the cartridge holder.

4. A device as in claim 3, wherein a distal region of the cylindrical body is enlarged to removably receive the cartridge connector.

5. A device as in claim 1, wherein the plunger driver is adjustable so that the length of travel of the piston rod can be selected prior to advancement of said piston rod.

6. A device as in claim 4, wherein the cartridge connector comprises a cylindrical body that is removably received within the enlarged distal region of the cartridge holder.

7. A device as in claim 2, wherein the sealed interior walls waste chamber is defined between spaced-apart walls in the cylindrical body of the cartridge connector.

8. A device as in claim 3, wherein a first end of the cylindrical body forms a cylindrical sleeve which surrounds the exposed ends of the exhaust cylindrical needle and the transfer needle, wherein said cylindrical sleeve is adapted to receive the septum end of a cartridge.

9. A device as in claim 8, wherein a first end of the transfer needle is axially spaced-apart from the first end of the exhaust needle.

10. A device as in claim 9, wherein the transfer needle passes axially through the sealed interior waste chamber.

11. A device as in claim 10, wherein an exposed second end of the transfer needle is free of surrounding structure, said connector further including a removable cap for placing over the exposed second end of the transfer needle.

12. A method for buffering an anesthetic cartridge, said method comprising:
   (a) removably inserting a first buffer cartridge having a septum and a plunger into a chamber of a cartridge holder;
   (b) attaching a plunger driver to a proximal end of the cartridge holder:
   (c) attaching one end of a cartridge connector to a distal end of the cartridge holder so that a transfer needle penetrates the septum of the buffer cartridge;
   (d) attaching a first anesthetic cartridge to another end of the cartridge connector so that the transfer needle and an exhaust needle penetrate the septum of the first anesthetic cartridge;
   (e) advancing a plunger on the plunger driver to engage the plunger on the buffer cartridge to transfer a volume of buffer from the first buffer cartridge into the first anesthetic cartridge and exhaust a volume of anesthetic from the first anesthetic cartridge;
   (f) removing the first anesthetic cartridge from the cartridge connector for use;
   (g) optionally connecting another anesthetic cartridge to the cartridge connector and repeating step (e) one or more times; and
   (h) when done with the first buffer cartridge, removing the plunger driver and the first buffer cartridge and cleaning the cartridge holder and plunger driver for re-use.

13. A method as in claim 12, further comprising disposing of the cartridge connector.

14. A method as in claim 13, wherein the cartridge connector contains the exhausted anesthetic.

15. A method as in claim 12, wherein additional anesthetic cartridges are sequentially replaced on the cartridge connector and volumes of buffer transferred to said additional anesthetic cartridges until the buffer cartridge is empty.

16. A method as in claim 15, further comprising visually observing the buffer cartridge to determine when said buffer cartridge is empty.

17. A method as in claim 16, wherein the cartridge holder has a window that allows visual observation of the contents of the buffer cartridge.

* * * * *